US009943286B2

(12) United States Patent
Shashar et al.

(10) Patent No.: US 9,943,286 B2
(45) Date of Patent: Apr. 17, 2018

(54) ULTRASONOGRAPHIC IMAGES PROCESSING

(71) Applicant: Tel HaShomer Medical Research Infrastructure and Services Ltd., Ramat-Gan (IL)

(72) Inventors: David Shashar, Ramat-Gan (IL); Reuven Achiron, Tel-Aviv (IL); Arnaldo Mayer, Ramat-HaSharon (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 199 days.

(21) Appl. No.: 14/405,204

(22) PCT Filed: Jun. 4, 2013

(86) PCT No.: PCT/IL2013/050480
§ 371 (c)(1),
(2) Date: Dec. 3, 2014

(87) PCT Pub. No.: WO2013/183051
PCT Pub. Date: Dec. 12, 2013

(65) Prior Publication Data
US 2015/0148657 A1 May 28, 2015

Related U.S. Application Data

(60) Provisional application No. 61/689,332, filed on Jun. 4, 2012.

(51) Int. Cl.
*A61B 8/14* (2006.01)
*A61B 5/00* (2006.01)
(Continued)

(52) U.S. Cl.
CPC .......... *A61B 8/0866* (2013.01); *A61B 5/7267* (2013.01); *A61B 8/0875* (2013.01);
(Continued)

(58) Field of Classification Search
None
See application file for complete search history.

(56) References Cited

U.S. PATENT DOCUMENTS

2005/0148852 A1  7/2005  Tank
2009/0082637 A1* 3/2009  Galperin .............. G06F 19/321
                                              600/300
(Continued)

FOREIGN PATENT DOCUMENTS

CN  1666710   9/2005
CN  1915177   2/2007
(Continued)

OTHER PUBLICATIONS

Notification of Office Action and Search Report dated Sep. 27, 2016 From the State Intellectual Property Office of the People's Republic of China Re. Application No. 201380034110.3 and Its Translation Into English.
(Continued)

*Primary Examiner* — Patricia Park

(57) ABSTRACT

A computerized method of adapting a presentation of ultrasonographic images during an ultrasonographic fetal evaluation. The method comprises performing an analysis of a plurality of ultrasonographic images captured by an ultrasonographic probe during an evaluation of a fetus, automatically identifying at least one location of at least one anatomical landmark of at least one reference organ or tissue or body fluid of the fetus in the plurality of ultrasonographic images based on an outcome of the analysis, automatically localizing a region of interest (ROI) in at least some of the
(Continued)

plurality of ultrasonographic images by using at least one predefined locational anatomical property of the at least one anatomical landmark, and concealing the ROI in a presentation of the at least some ultrasonographic images during the evaluation. At least one anatomical landmark is imaged in the presentation and not concealed by the ROI.

20 Claims, 23 Drawing Sheets
(23 of 23 Drawing Sheet(s) Filed in Color)

(51) Int. Cl.
    *A61B 8/00*     (2006.01)
    *G06T 15/00*     (2011.01)
    *A61B 8/08*     (2006.01)
    *G06T 7/73*     (2017.01)

(52) U.S. Cl.
    CPC ............ *A61B 8/4444* (2013.01); *A61B 8/463* (2013.01); *A61B 8/469* (2013.01); *A61B 8/483* (2013.01); *A61B 8/52* (2013.01); *A61B 8/523* (2013.01); *A61B 8/5223* (2013.01); *G06T 7/73* (2017.01); *G06K 2209/051* (2013.01); *G06T 2207/10016* (2013.01); *G06T 2207/10132* (2013.01); *G06T 2207/10136* (2013.01); *G06T 2207/20081* (2013.01); *G06T 2207/20084* (2013.01); *G06T 2207/30044* (2013.01)

(56) References Cited

U.S. PATENT DOCUMENTS

2009/0169074 A1* 7/2009 Avinash ................ G06F 19/321
    382/128

2011/0255762 A1* 10/2011 Deischinger ........... A61B 8/463
    382/131
2011/0257529 A1* 10/2011 Casciaro .............. A61B 8/0866
    600/443

FOREIGN PATENT DOCUMENTS

| CN | 101081168 | 12/2007 |
|---|---|---|
| CN | 201076477 | 6/2008 |
| CN | 102048557 | 5/2011 |
| CN | 104622495 | 5/2015 |
| WO | WO 2013/183051 | 12/2013 |

OTHER PUBLICATIONS

Notification of Office Action dated Nov. 24, 2015 From the State Intellectual Property Office of the People's Republic of China Re. Application No. 201380034110.3.
Notification of Office Action dated Mar. 30, 2017 From the State Intellectual Property Office of the People's Republic of China Re. Application No. 201380034110.3. (4 Pages).
Translation Dated Dec. 10, 2015 of Notification of Office Action dated Nov. 24, 2015 From the State Intellectual Property Office of the People's Republic of China Re. Application No. 201380034110. 3.
International Preliminary Report on Patentability dated Dec. 18, 2014 From the International Bureau of WIPO Re. Application No. PCT/IL2013/050480.
International Search Report and the Written Opinion dated Sep. 12, 2013 From the International Searching Authority Re. Application No. PCT/IL2013/050480.

* cited by examiner

ULTRASONOGRAPHIC IMAGES PROCESSING

RELATED APPLICATIONS

This application is a National Phase of PCT Patent Application No. PCT/IL2013/050480 having International filing date of Jun. 4, 2013, which claims the benefit of priority under 35 USC § 119(e) of U.S. Provisional Patent Application No. 61/689,332, filed on Jun. 4, 2012. The contents of the above applications are all incorporated by reference as if fully set forth herein in their entirety.

BACKGROUND

The present invention, in some embodiments thereof, relates to medical imaging adjustment and, more particularly, but not exclusively, to system and method of adjusting ultrasonographic images of fetal anatomy.

Ultrasound (US) screening during pregnancy is used to identify fetal anatomical anomalies and malformations. This has become common practice worldwide. In certain south east Asian countries, the increase in ultrasound portability, decrease in cost and increase in accuracy has led to its exploitation for gender determination to be used for sex selective abortions. This has caused significant gender ratio differences with long lasting effects, which bring about serious national social problems.

SUMMARY

According to an aspect of some embodiments of the present invention there is provided a computerized method of adapting a presentation of ultrasonographic images during an ultrasonographic fetal evaluation. The method comprises performing an analysis of a plurality of ultrasonographic images captured by an ultrasonographic probe during an evaluation of a fetus, automatically identifying at least one location of at least one anatomical landmark of at least one reference organ or tissue or body fluid of the fetus in the plurality of ultrasonographic images based on an outcome of the analysis, automatically localizing a region of interest (ROI) in at least some of the plurality of ultrasonographic images by using at least one predefined locational anatomical property of the at least one anatomical landmark, concealing the ROI in a presentation of the at least some ultrasonographic images during the evaluation. The at least one anatomical landmark is imaged in the presentation and not concealed by the ROI.

Optionally, the ROI includes an image portion depicting the genitalia of the fetus.

Optionally, the method further comprises providing an anatomical dataset associating between a plurality of predefined locational anatomical properties and a plurality of anatomical landmarks; wherein the automatically localizing comprises selecting the predefined locational anatomical property from the plurality of predefined locational anatomical properties.

Optionally, the presentation is rendered while the ultrasonographic probe is manually maneuvered.

Optionally, the automatically identifying comprises identifying, from the plurality of ultrasonographic images, a group of ultrasonographic images wherein each member images a genital plan; the at least some ultrasonographic images are selected from the group.

More optionally, the automatically identifying comprises identifying the at least one anatomical landmark in each member of the group.

More optionally, each member of the group is identified by: segmenting a plurality of objects in the plurality of ultrasonographic images, identifying a plurality of anatomical features of each the object, substituting the plurality of anatomical features in a dataset, and classifying the member based on an analysis of the dataset.

More optionally, the classifying is performed by a classifier created by at least one classifier trained by supervised learning of a presence or absence of the at least one anatomical landmark.

More optionally, the classifying is performed by a plurality of classifiers set to calculate a score indicative of an estimate of a presence or absence of the at least one anatomical landmark.

More optionally, the automatically identifying is performed by calculating a form factor of at least one object depicted in the plurality of ultrasonographic images.

More optionally, the automatically identifying is performed by calculating a convexity of at least one object depicted in the plurality of ultrasonographic images.

More optionally, the automatically identifying is performed by calculating a contour complexity of at least one object depicted in the plurality of ultrasonographic images.

More optionally, the automatically identifying is performed by calculating texture descriptors of at least one object depicted in the plurality of ultrasonographic images.

Optionally, the at least one anatomical landmark comprises a plurality of anatomical landmarks.

More optionally, the automatically localizing is performed by a combination of a plurality of predefined locational anatomical properties taken from the plurality of anatomical landmarks.

Optionally, the predefined locational anatomical property is a range of distances between the at least one anatomical landmark and the genitalia of the fetus.

Optionally, the at least one anatomical landmark comprises a plurality of anatomical landmarks; further comprising calculating an intersection between a plurality of distance ranges each between one of the plurality of anatomical landmarks and the genitalia of the fetus; wherein the automatically localizing is based on the location of the intersection.

Optionally, the at least one anatomical landmark is at least one femur.

Optionally, the at least one anatomical landmark is at least one thigh.

Optionally, the at least one anatomical landmark is the pelvis.

Optionally, the at least one anatomical landmark is the spine.

Optionally, the at least one anatomical landmark is the U shape of thighs and pelvis.

Optionally, the at least one anatomical landmark is the anterior contour of the trunk.

Optionally, the at least one anatomical landmark is the urinary bladder.

Optionally, the at least one anatomical landmark is at least one of the pelvic bones including the Ischium, Pubis, Ilius or Sacrum bones.

Optionally, the at least one anatomical landmark is amniotic fluid.

Optionally, the at least one anatomical landmark is the umbilical cord.

Optionally, the concealing is performed by at least one of the following: editing, masking, blurring, darkening, coloring, extracting, removing, trimming or manipulating.

Optionally, the concealing comprises adding an overlay covering the region of interest to the plurality of ultrasonographic images.

Optionally, the ultrasonographic images are slices from a stack used for three dimensional or four dimensional ultrasonographic imaging.

Optionally, the ROI is a volume and the ultrasonographic images are volumetric ultrasonographic images.

According to an aspect of some embodiments of the present invention there is provided a system of adapting a presentation of ultrasonographic images during an ultrasonographic fetal evaluation. The system comprises an interface which receives a plurality of ultrasonographic images captured by an ultrasonographic probe performing an evaluation of a fetus of a patient, a computerized processor, and a memory which comprises instructions to perform using the computerized processor, and an analysis of a plurality of ultrasonographic images captured by an ultrasonographic probe during an evaluation of a fetus, to identify at least one anatomical landmark of at least one reference organ or tissue or body fluid of the fetus based on an outcome of the analysis, to localize, based on at least one predefined locational anatomical property or texture descriptor of the at least one anatomical landmark, a region of interest (ROI) in the plurality of ultrasonographic images, and to conceal the ROI in a presentation of at least some of the plurality of ultrasonographic images during the evaluation. The at least one anatomical landmark is imaged in the presentation and not concealed by the ROI.

According to an aspect of some embodiments of the present invention there is provided a computerized method of concealing a portion of an ultrasonographic image depicting genitalia of a fetus during an ultrasonographic fetal evaluation. The method comprises providing an anatomical dataset which is indicative of at least one predefined locational anatomical property of each of a plurality of anatomical landmarks of at least one reference organ or tissue or body fluid of the fetus, performing an analysis of a plurality of ultrasonographic images captured by an ultrasonographic probe during an evaluation of a fetus, selecting a group of ultrasonographic images from the plurality of ultrasonographic images such that each group member of the group depicts at least one of the plurality of anatomical landmarks, localizing, in each group member of the group, a genital region of interest (ROI) which images the genitalia of the fetus, the localizing is performed according to respective the at least one predefined locational anatomical property of respective the at least one anatomical landmark imaged in the member, and concealing the ROI in a presentation of each member of the group during the evaluation. The at least one anatomical landmark is imaged in the presentation and not concealed by the ROI.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a system of adapting a presentation of ultrasonographic images during an ultrasonographic fetal evaluation, according to some embodiments of the present invention;

FIG. 2 is a flowchart of a computerized method of concealing a genital ROI in ultrasonographic images which are presented during an ultrasonographic fetal evaluation, for example using the system depicted in FIG. 1, according to some embodiments of the present invention;

FIG. 3 is a flowchart of process for determining whether an ultrasonographic image images a genital plane, according to some embodiments of the present invention;

FIG. 4 is a set of images each depicting an exemplary processed version of the ultrasonographic image during different stages of an exemplary segmentation, according to some embodiments of the present invention;

FIGS. 5 and 6 are schemes depicting the substituting of values of features from two different labeled (segmented) objects in two different feature vectors, according to some embodiments of the present invention;

FIG. 7 is a schematic illustration of a process of placing points in an object space based on a feature dataset, according to some embodiments of the present invention;

FIG. 8 is a schematic illustration of an object space, according to some embodiments of the present invention;

FIG. 9 is a flowchart depicting how valued scores given to an ultrasonographic image by classifiers of anatomical landmarks are combined to form a score vector that is used by a combination function to classify ultrasonographic image, according to some embodiments of the present invention;

FIG. 10 is a schematic illustration depicting distance ranges from the urinary bladder, the left femur, and the right femur by pairs of aligned curved lines and an intersection of these distance ranges, according to some embodiments of the present invention;

FIGS. 11A-11C are schematic illustrations of distance ranges from the left femur, the right femur and the urinary bladder;

FIG. 11D is a schematic illustration depicting the ultrasonographic image and the intersection of areas defined by different distance ranges from different anatomical landmarks;

Figure 11C:
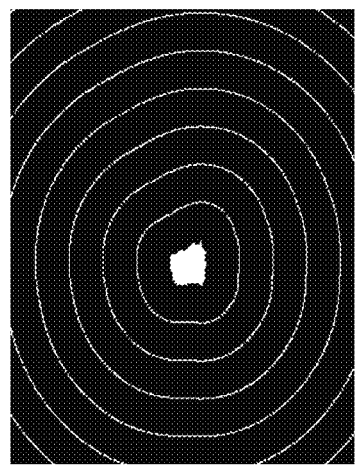
Figure 11B:
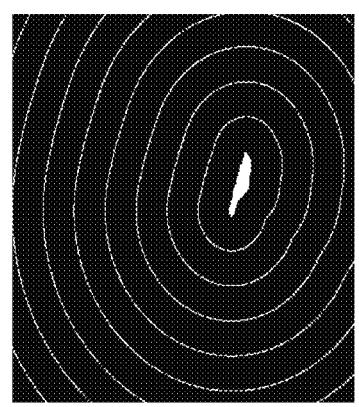
Figure 11A:
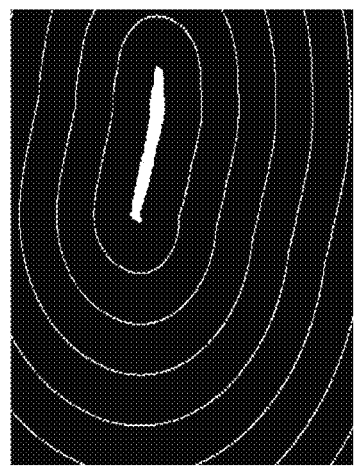
Figure 11D:
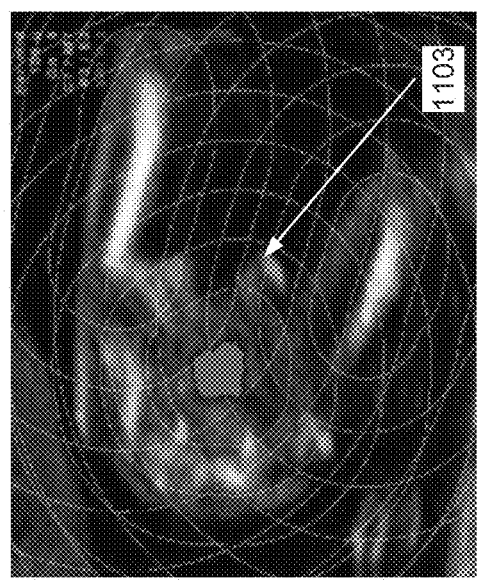
Figure 11E:
Figure 12A:
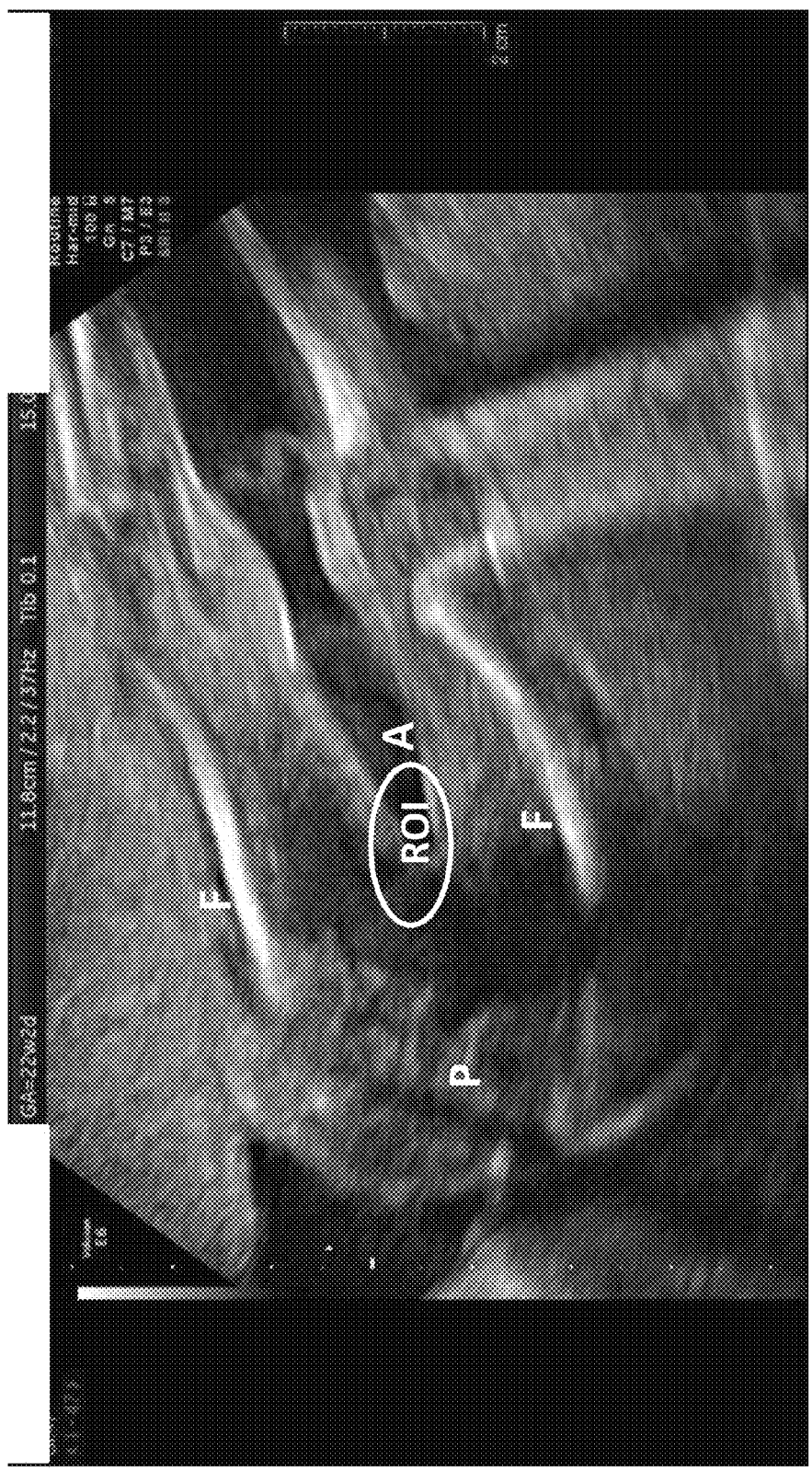
Figure 12B:
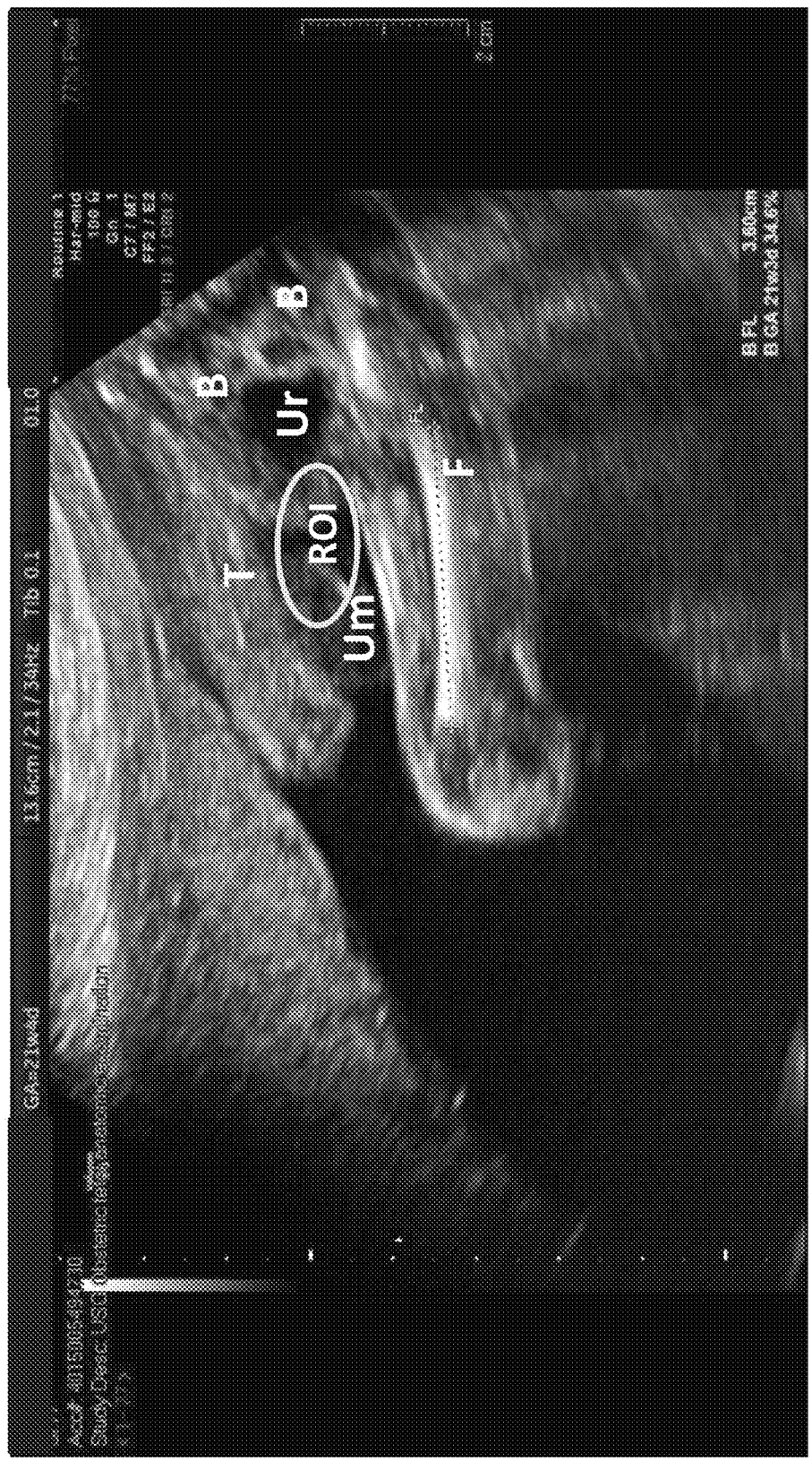
Figure 12C:
Figure 12D:
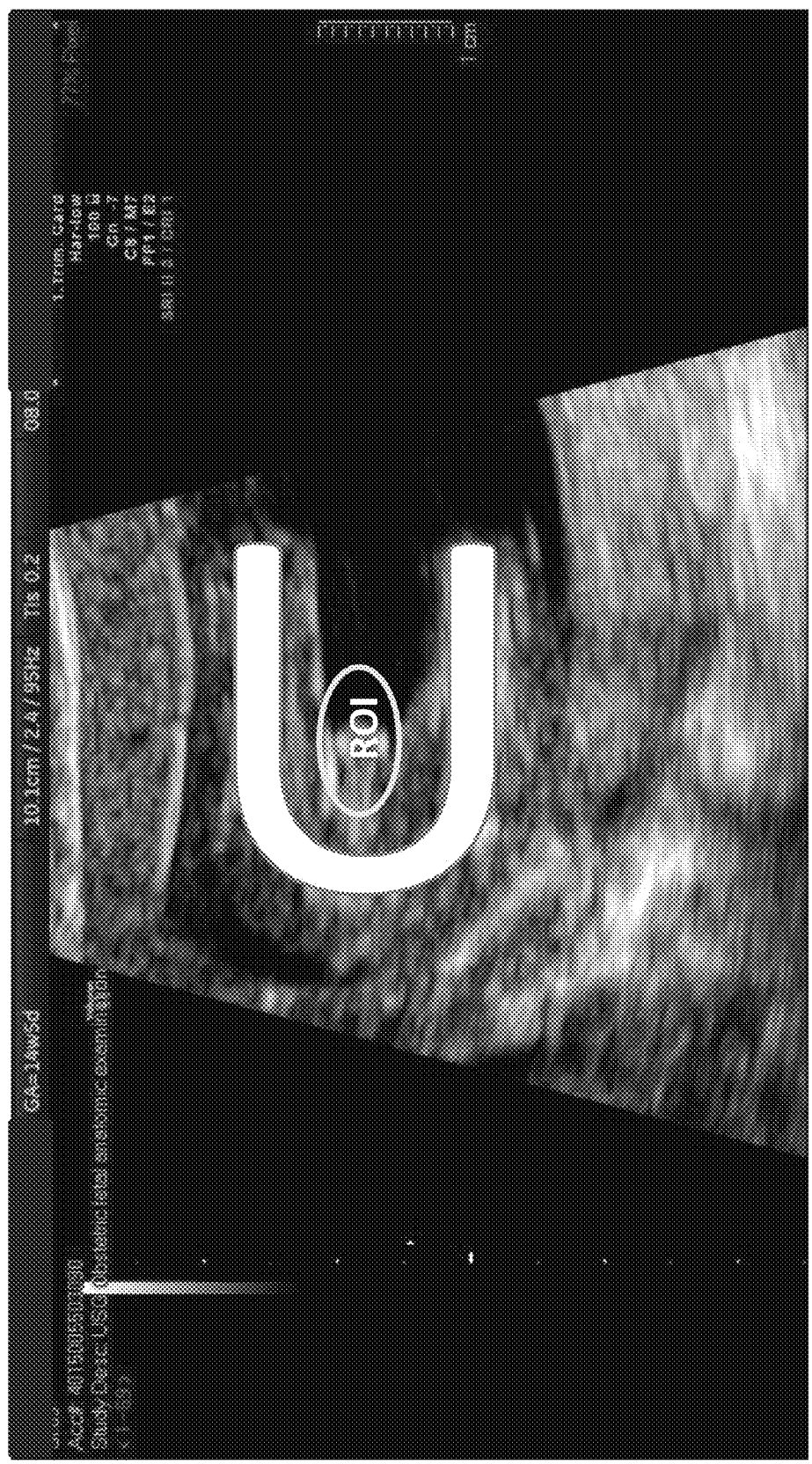
Figure 12E:
Figure 13A:
Figure 13B:
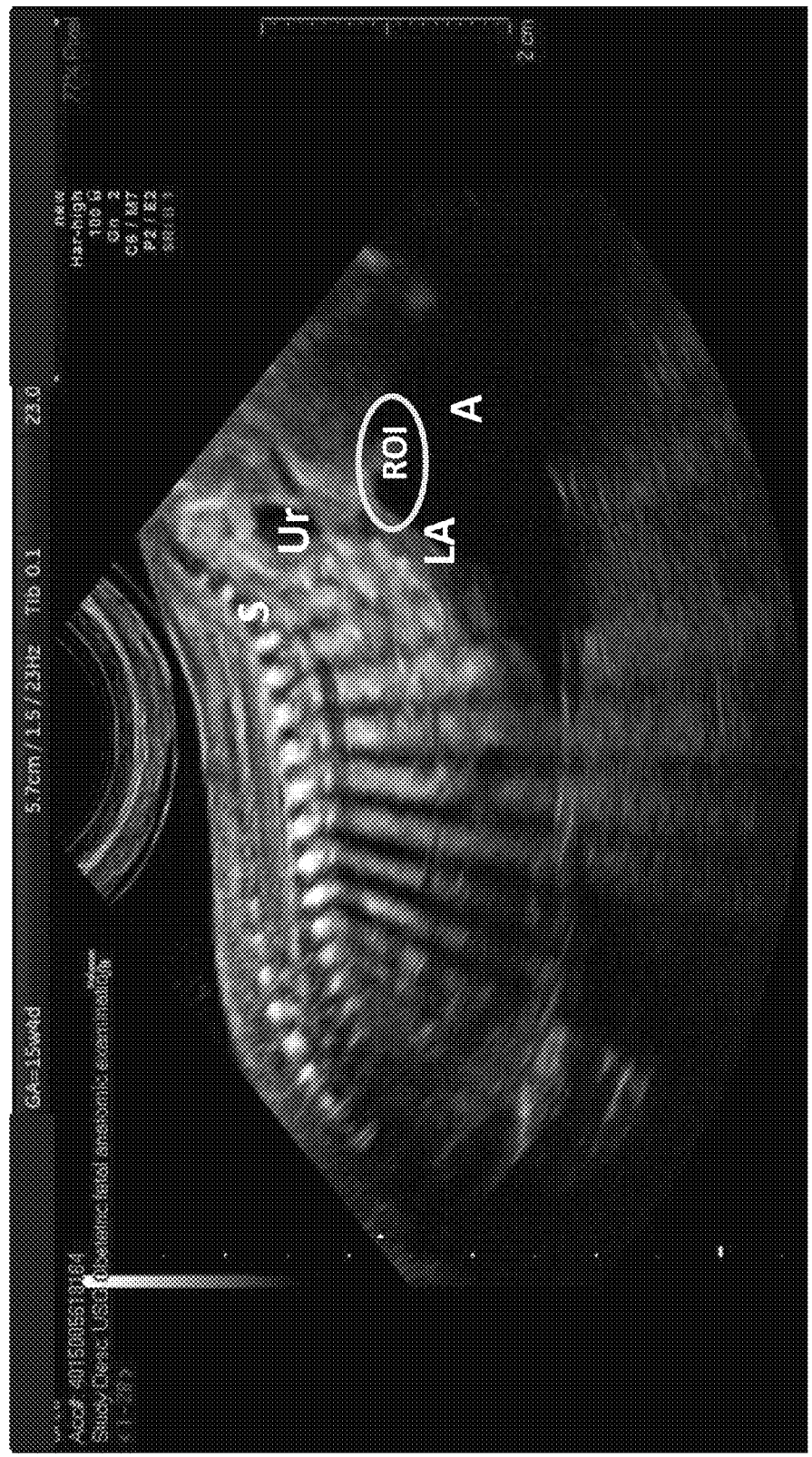
Figure 13C:
Figure 14A:
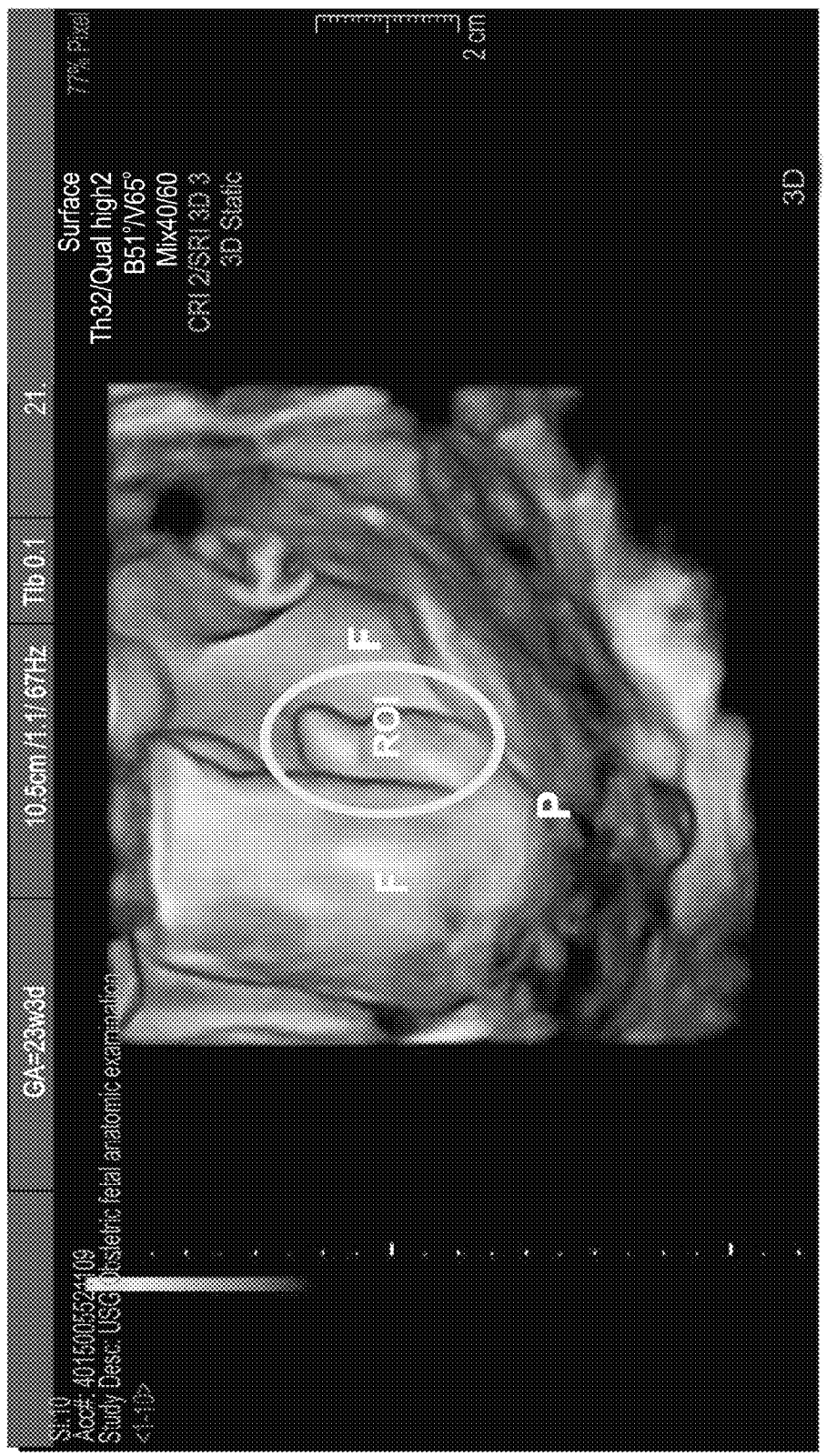
Figure 14B:
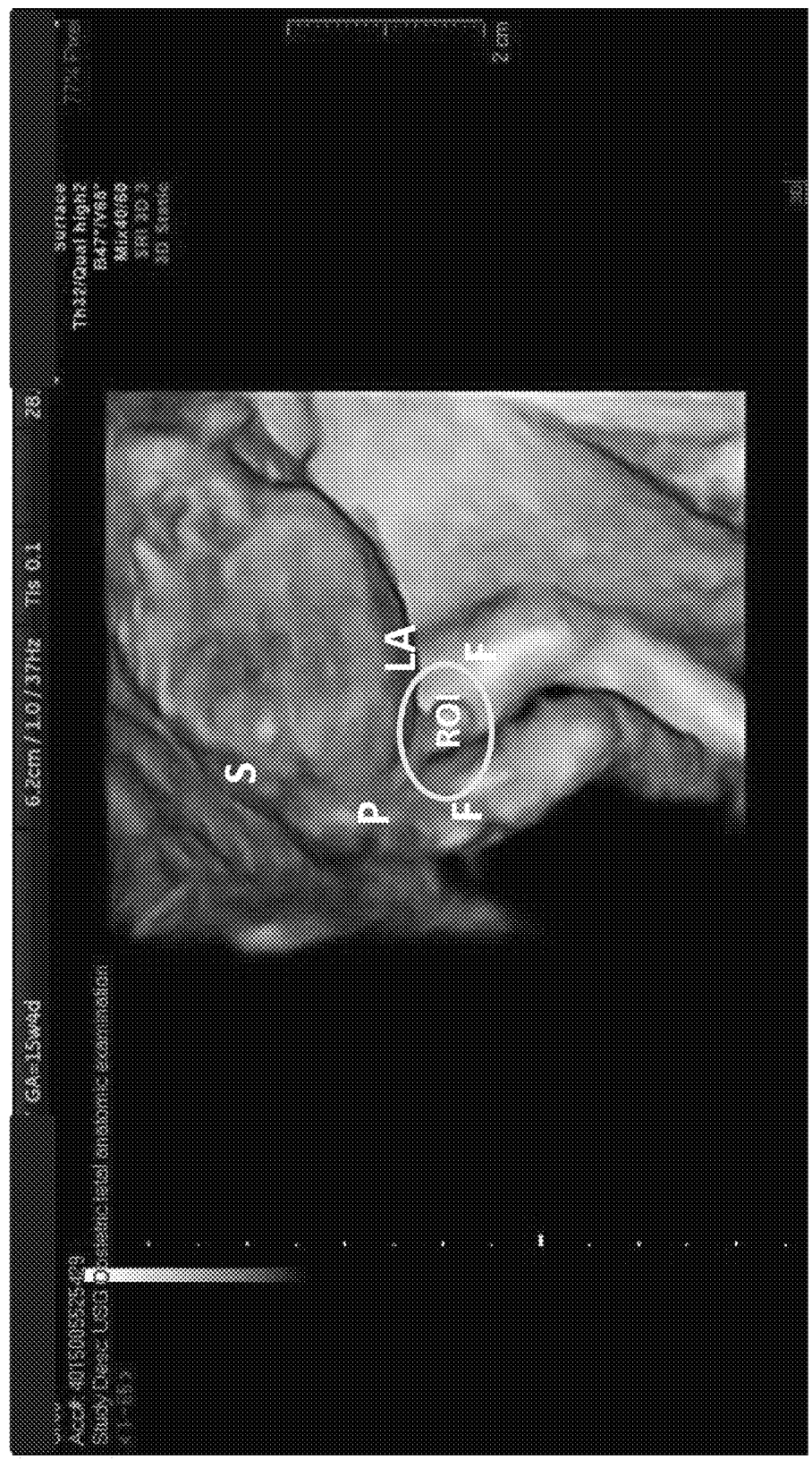
Figure 14C:

FIG. 11E is a schematic illustration depicting the genital ROI that is calculated based on the location of the intersection;

FIGS. 12A-12E are exemplary ultrasonographic images depicting a coronal/tangential view of the genital ROI and anatomical landmarks, according to some embodiments of the present invention;

FIGS. 13A-13C are exemplary ultrasonographic images depicting a midsagittal view of the genital ROI and anatomical landmarks, according to some embodiments of the present invention; and FIGS. 14A-14C are additional exemplary ultrasonographic images depicting 3D views of the genital ROI and anatomical landmarks.

DETAILED DESCRIPTION

The present invention, in some embodiments thereof, relates to medical imaging adjustment and, more particularly, but not exclusively, to system and method of adjusting ultrasonographic images of fetal anatomy.

According to some embodiments of the present invention there are provided methods and systems for concealing an image portion, such as a genital image portion, in an ultrasonographic image where the location of the image portion is calculated according to predefined locational anatomical property(ies) of one or more anatomical landmarks identified and localized in the ultrasonographic image and will not be concealed. This image portion is referred to herein as a genital region of interest (ROI). For example, anatomical landmarks are optionally identified by segmenting and classifying image objects in the ultrasonographic image. The image objects are optionally classified according to their structural features, for example form factor, convexity, contour complexity, and/or intensity histogram moment(s) and/or their characteristics as echoic, hypoechoic, or hyperechoic, for instance as described below. In such embodiments, the location of the concealed ROI is calculated without actually processing the image portion that images the ROI and/or directly identifying its location. For example, the ROI is located based on anatomical knowledge about the expected range of distances between the organ(s) in the ROI, for instance the genitalia, and the detected anatomical landmarks are non genital anatomical landmarks which remain unconcealed when the ultrasonographic image is presented. This concealment may be repeated for a plurality of images and/or used as a preliminary process after which the ROI is tracked by a tracking method, for example as known in the art. Optionally, a set of predefined distances from a number of different anatomical landmarks are substituted in a function, together with the estimated location of the different anatomical landmarks, for determining the location of the ROI.

The ultrasound methods and systems which are outlined above and described below allow a physician to perform a full fetal evaluation, for example second and third trimester fetal anatomy screening, without being exposed to the gender of the fetus. In such a manner, the output of respective ultrasound systems does not allow using these ultrasound systems for gender diagnosis to be used for a gender-selective abortion.

Gender selective abortion causes significant gender ratio differences with long lasting effect in several countries. In some countries laws have been enacted to prevent the use of Ultrasound for gender determination. The enforcement of these laws can be done by requiring the usage of ultrasonic systems with a mechanism that conceals an image portion imaging the genitalia of a fetus in an ultrasonographic image presented during an ultrasonographic fetal evaluation.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 1:
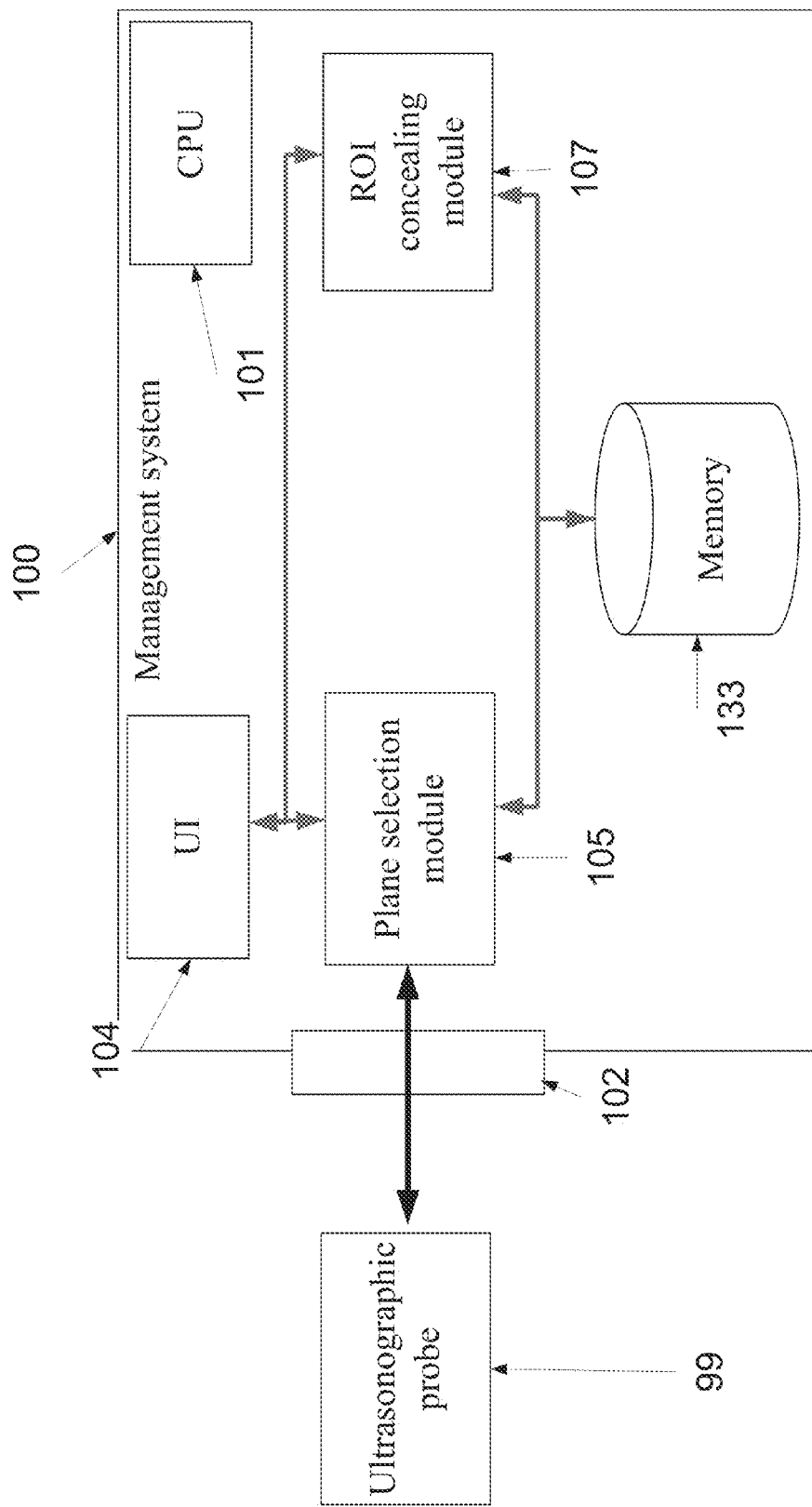

Reference is now made to FIG. 1, which is a system 100 of adapting a presentation of ultrasonographic images during an ultrasonographic fetal evaluation, according to some embodiments of the present invention. The system 100 may be implemented using a computing unit that includes a processor 101, a probe interface 102, a presentation unit, such as a screen, and a memory 133. The interface device 102 is set to receive a plurality of ultrasonographic images from an ultrasonographic probe 99 used to perform evaluation of a fetus. The ultrasonographic probe 99 may be a two-dimensional (2D) layout ultrasonographic probe, a three dimensional (3D) or four dimensional (4D) ultrasonographic probe, an arc layout ultrasonographic probe and/or any other probe which may be used for capturing fetal images. Although most of the examples herein refer to 2D ultrasonographic images, the term ultrasonographic images includes 2D ultrasonographic images, 3D ultrasonographic images, ultrasonographic slices of 3D images, 4D ultrasonographic images and Doppler US images. Adjustment of the embodiments described herein to process 3D and 4D ultrasonographic images is known in light of the below teaching.

The system 100 may be an adapted version of an ultrasound system such as ClearVue 350/550/650 ultrasound system of Philips™ or any other ultrasound system suitable for fetal evaluation.

Optionally, the system 100 further comprises a user interface (UI) 104 with a presentation unit that receives instructions from a user, for example via a man machine interface (MMI) unit that includes a keyboard, a mouse, a touch screen, and/or the like, and a presentation unit for displaying, among others, the images of the plurality of ultrasonographic images, for example a liquid crystal display (LCD).

The system 100 further includes a plane selection module 105 which identifies ultrasonographic images depicting genital fetal scan planes from the ultrasonographic images. A genital plane is an ultrasonographic image imaging a fetal scan plane that allows a human observer viewing the ultrasonographic image to determine accordingly the gender of the imaged fetus, for example through an anterior (coronal) plane, a profile (mid-sagittal) plane, and a posterior view (tangential position) plane. The genital plane may be captured in a two dimensional view in an anterior upfront view (coronal), profile view (midsagital or parasagital) or a posterior view of the buttock when the thighs are flexed (tangential position). The density, position, size, structure, configuration, and/or shape and/or echogenicity of an anatomical landmark depicted in these plans, for example the femur bones and/or the urinary bladder as those relate to the pelvis, are used to locate the ROI.

Optionally, the plane selection module 105 identifies an ultrasonographic image depicting a genital plane using a classifier that classifies features of image objects detected in the ultrasonographic image and/or by comparing the ultrasonographic image with reference maps stored in a database to identify a match. Optionally, the system 100 includes an ROI concealing module 107 which conceals the genital ROI in the ultrasonographic images identified as depicting a genital fetal scan plane. The concealing is performed by editing, masking, blurring, darkening, coloring, extracting, removing, trimming or manipulating and/or otherwise concealing the genital ROI. The concealed ultrasonographic images are optionally a variation of the original ultrasonographic images wherein the genital ROI is edited in a manner that does not allow a human observer to determine the gender of the fetus.

The ROI concealing module 107 localizes anatomical landmarks, which are non genital reference organs or tissues or body fluids, in the ultrasonographic images identified as imaging a genital fetal scan plane. This allows localizing the genital ROI in relation to the non genital reference organs or tissues or body fluids (which for brevity also include organs portions). In these embodiments, the genital ROI may be concealed based on indirect localization performed without direct localization of the genital ROI and by direct localization of anatomical landmark which are out of the genital ROI. Exemplary anatomical landmarks are: left femur, right femur, left and right femur, left thigh, right thigh, left and right thigh, the urinary bladder, pelvis, the pelvic bone including the Ischium, Pubis, Ilius or Sacrum bones, U shape of thighs and pelvis, spine, anterior contour of the trunk, amniotic fluid, and umbilical cord.

The concealment allows the system 100 to present concealed ultrasonographic images that let an operator, for example a physician, to perform a fetal anatomy screening, for example second and third trimester fetal anatomy evaluation, nuchal translucency, a doppler study, a heart echo, a biophysical profile, an estimation of fetal weight and/or the like without being exposed to the gender of the fetus.

The concealed ultrasonographic images may be presented to the operator by a client terminal, such as a personal computer, a PDA, a Smartphone, a thin client, a laptop and the like.

Figure 2:
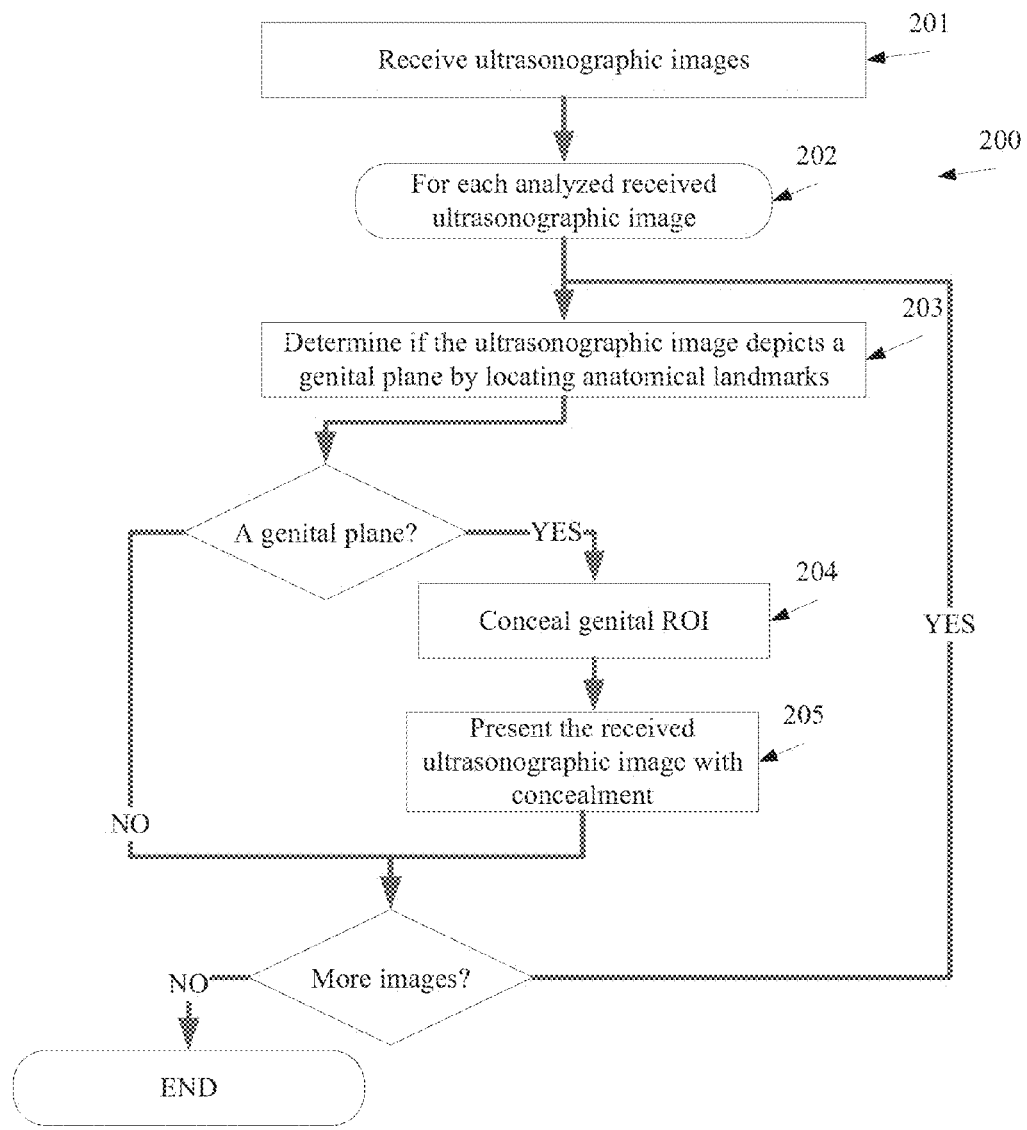

Reference is also now made to FIG. 2, which is a flowchart 200 of a computerized method of concealing the genital ROI in ultrasonographic images which are presented during an ultrasonographic fetal evaluation, for example using the system 100 depicted in FIG. 1, according to some embodiments of the present invention.

First, as shown at 201, ultrasonographic images captured during an ultrasonographic fetal evaluation are received from a probe, such as the ultrasound probe 99 in FIG. 1. For example, a human operator, such as a technician or a physician, manually maneuvers the ultrasonographic probe on the abdomen of a pregnant woman or vaginally. Similarly to the commonly known in the art, the ultrasonographic images which are captured by the ultrasonographic probe, are presented to the operator, for example on the presentation unit of the UI 104 in FIG. 1. The probe may be automatically maneuvered by a robotic hand. As shown at 201, the plurality of ultrasonographic images, which are captured by the ultrasonographic probe 99 in FIG. 1 during the organ evaluation of a fetus, are received by the input unit 202.

Now, some or all of the ultrasonographic images are analyzed. For each one of the analyzed ultrasonographic images 203-205 are performed.

First, as shown at 203, an analysis of the ultrasonographic image is performed to determine whether the ultrasonographic image depicts a genital plane. For example, the genital plane is identified by labeling a plurality of anatomical objects in the ultrasonographic image and substituting values in a feature vector accordingly, facilitating the identification of anatomical landmarks by supervised classifiers.

Figure 3:
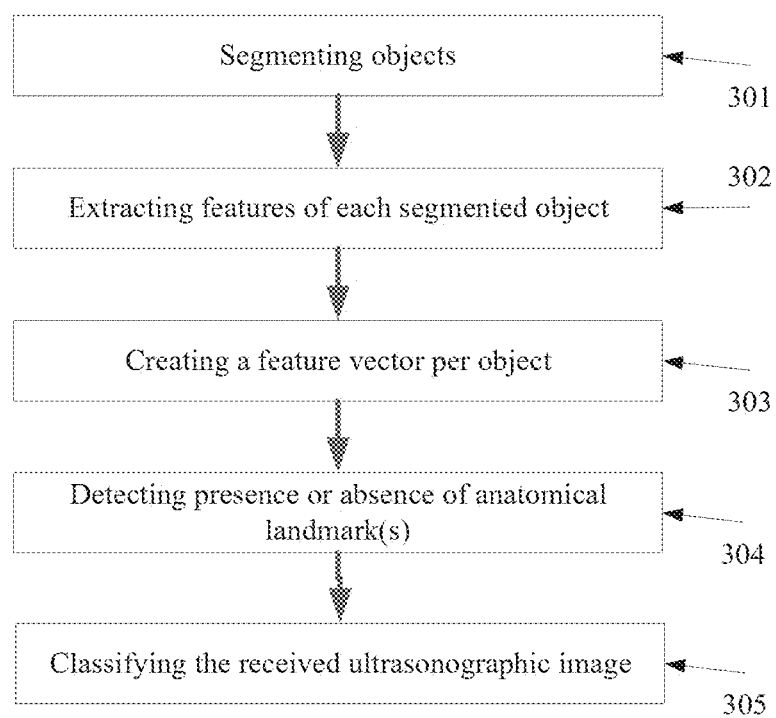
Figure 4:
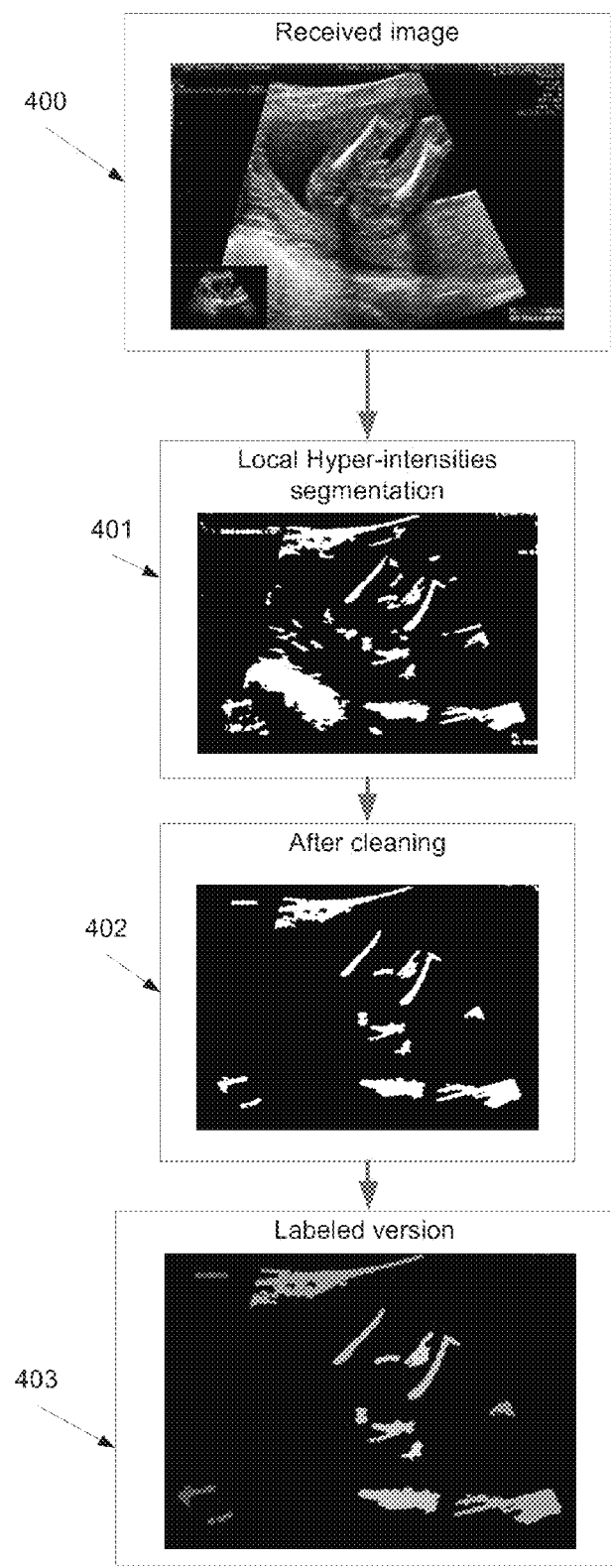

For example, reference is now made to FIG. 3 which is a flowchart of process for determining whether an ultrasonographic image images a genital plane, according to some embodiments of the present invention. First, as shown at 301, objects in the ultrasonographic image are segmented, for example by a local hyperintensities or hyperechoic segmentation. Optionally, one or more filters are used for cleaning the segmented image. For instance, reference is also made to FIG. 4 which is a set of images each depicting an exemplary processed version of the ultrasonographic image during different stages of an exemplary segmentation, according to some embodiments of the present invention. The set of images includes: an exemplary ultrasonographic image 400, an output 401 of a local Hyperintensities segmentation of the ultrasonographic image, an output 402 of cleaning the output 401, for example by filtering objects based on size and/or shape, for instance anatomical thresholds and/or templates, and a labeled version of the exemplary ultrasonographic image 400 based on output 403 wherein each object is labeled differently (with each label represented by a different colors). This creates a set of segmented objects.

Now, as shown at 302, a plurality of features are extracted from each segmented object. For example as shown in FIG. 5.

One or more of the following anatomical features are calculated per object:
a form factor, for instance width (a) length (b) ratio (a/b);
convexity, for instance by dividing the total area of the object with the area of its convex hull;
contour complexity, for example by dividing the perimeter of the object with 2(a+b);
intensity histogram moments, for example by calculating the intensity histogram first two moments for the pixels belonging to the segmented object, that is mean and standard deviation; and
the texture descriptors as computed, for example, by Gabor filters that convolve the object intensity with a bank of filters Gabor filters may be obtained by modulating a Gaussian kernel function by a sinusoidal plane wave at various scales and orientations.

Figure 5:
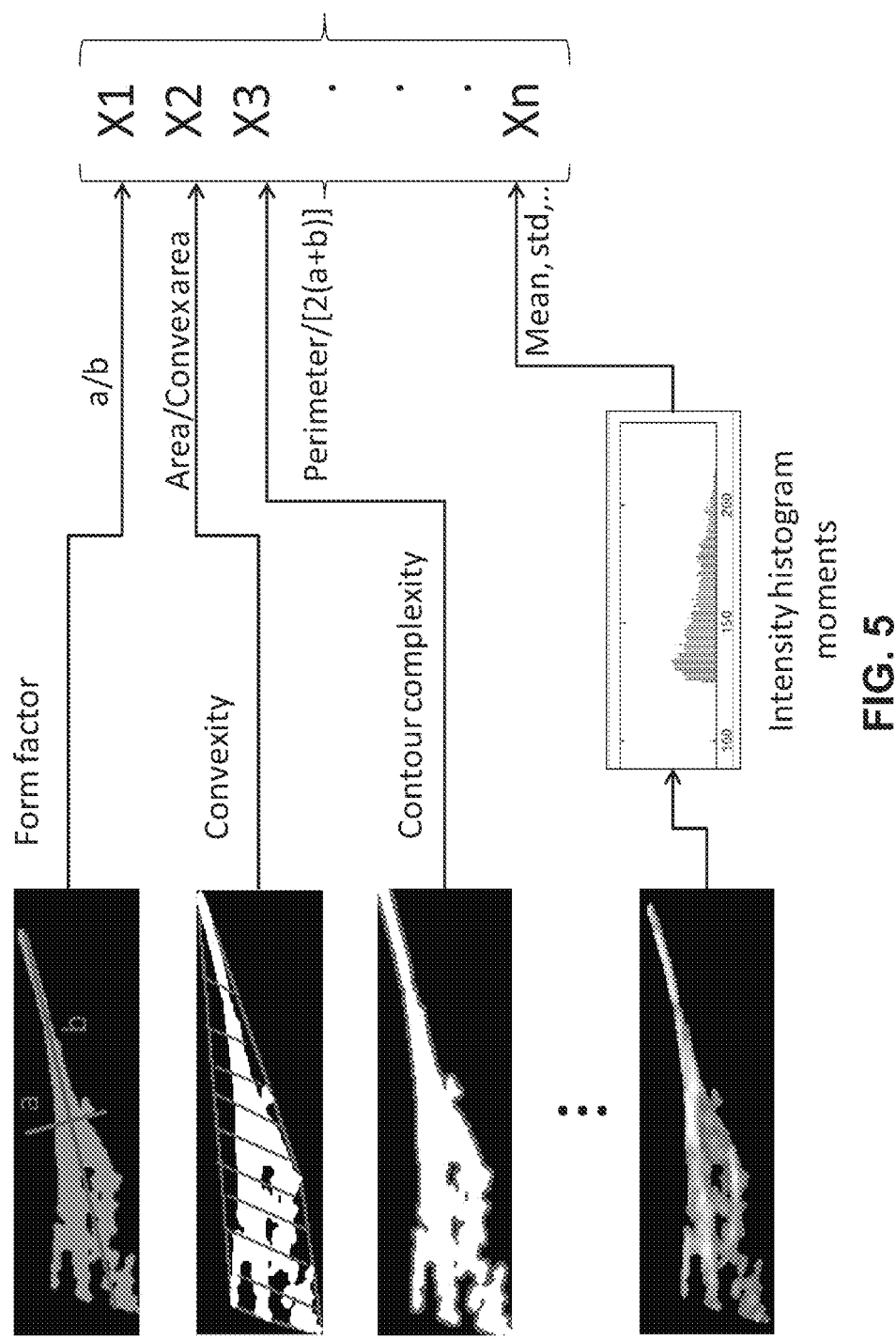
Figure 6:
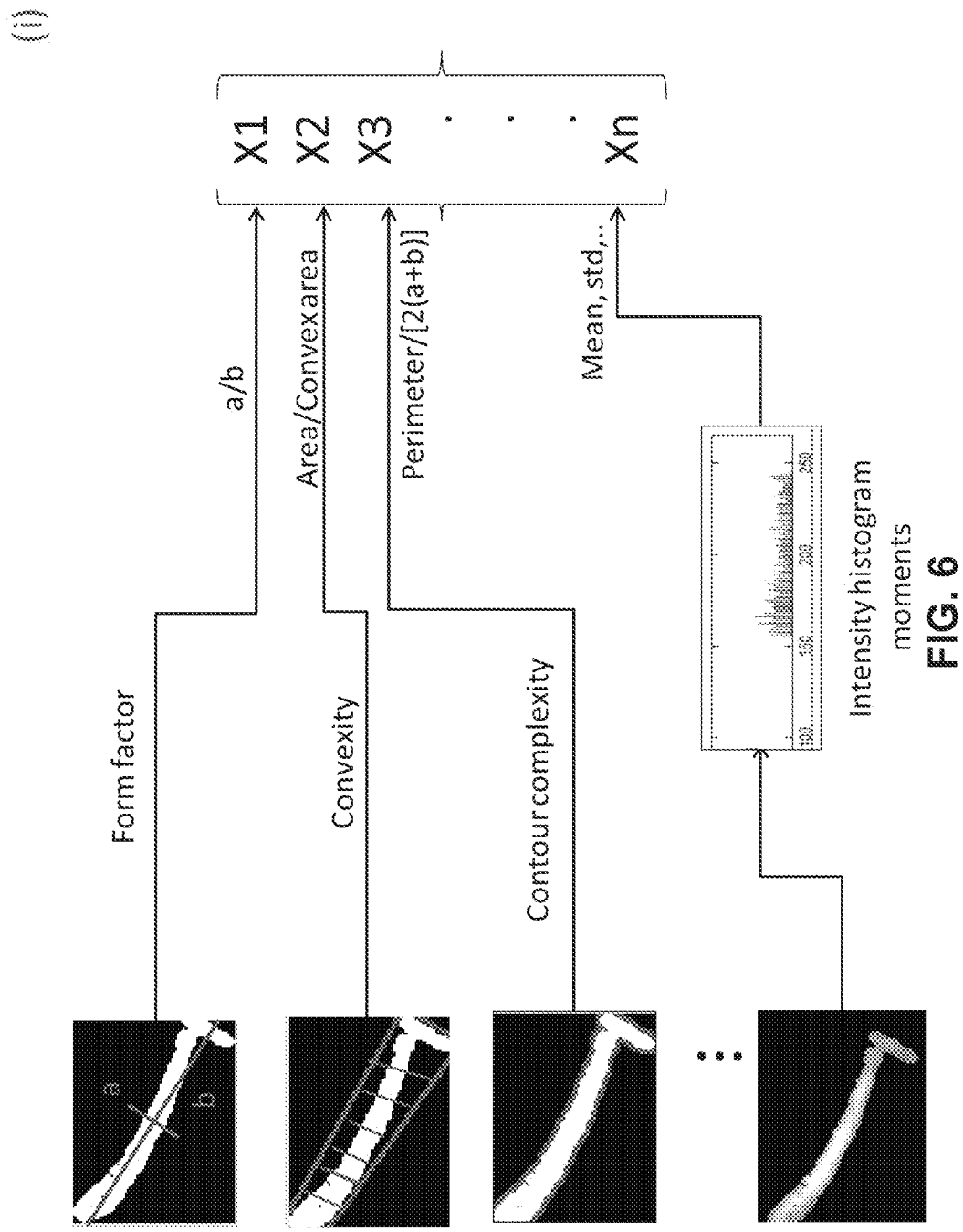

For instance, FIGS. 5 and 6 are schemes depicting the substituting of values of features from two different labeled (segmented) objects in two different feature vectors, according to some embodiments of the present invention.

Figure 7:
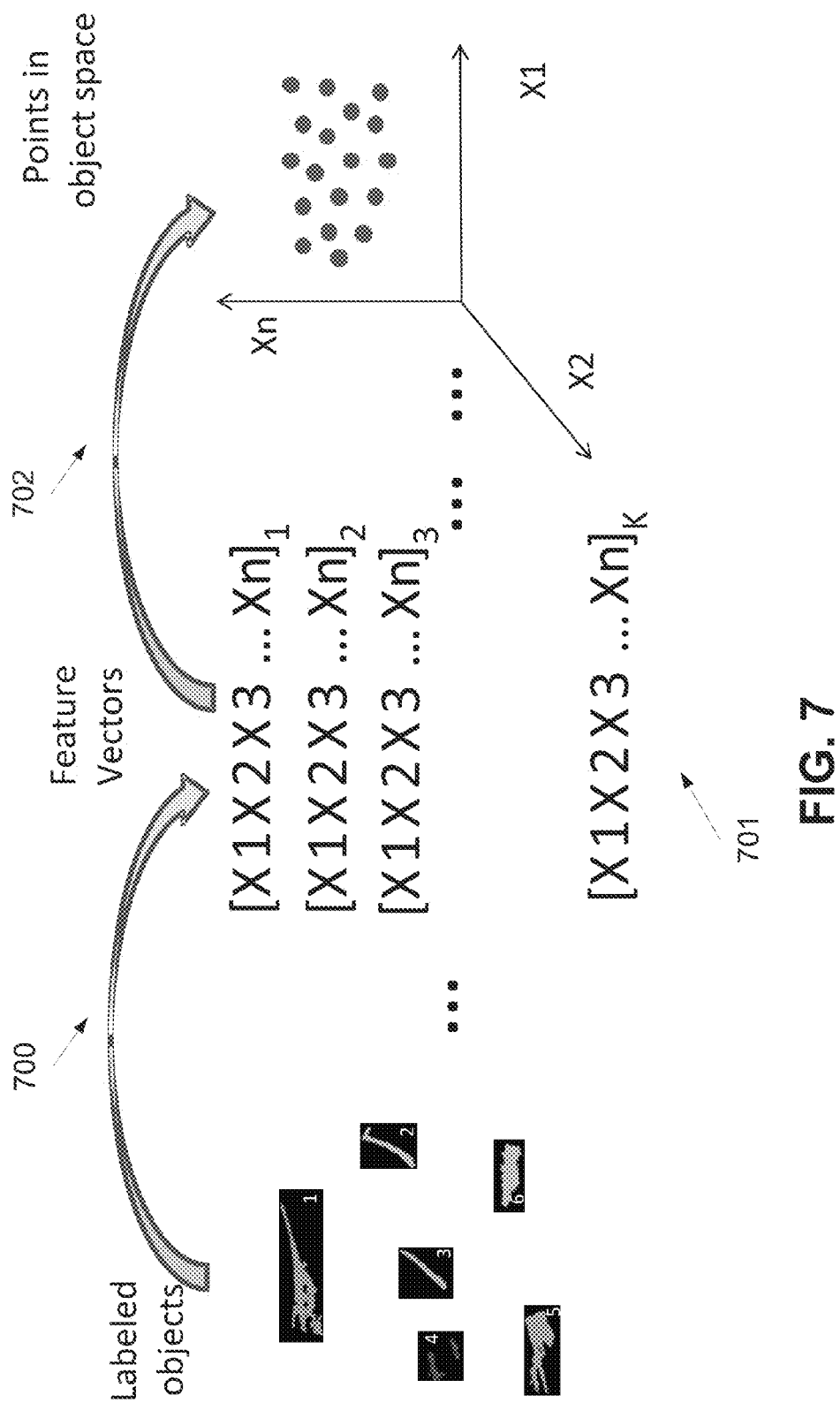

As shown at 303 and schematically illustrated by numeral 700 of FIG. 7, the extracted features are logged for example added to a feature dataset, for example a matrix. For instance, features of each segmented object are inputted to a different feature vector and the feature vectors of all segmented objects may be appended to form a matrix as illustrated by numeral 701 in FIG. 7.

Now, as shown at 305, the ultrasonographic image is classified as a genital plan based on the presence or absence of one or more anatomical landmarks and/or the anatomical landmark value of the objects.

Optionally, the feature vectors from the matrix are analyzed to classify the segmented objects, facilitating the detection of one or more anatomical landmarks in the ultrasonographic image.

The classification may be binary or valued, for instance given an anatomical landmark value (rank/score) between 0 and 1. A classifier, referred to herein as an anatomical landmark classifier, may be for example any of the following classifiers: a support vector machine (SVM) classifier, a decision tree classifier, a K nearest neighbors (KNN) classifier, a linear discriminate analysis (LDA) classifier, an adaptive boosting (ADABOOST) classifier, an artificial neural network (ANN) classifier, and/or a set of heuristic rules, for example rules which are manually adapted.

Optionally, the feature dataset is processed by a plurality of classifiers to identify which of a plurality of anatomical landmarks appears in the ultrasonographic image.

For example, as illustrated by numeral 702 of FIG. 7, each feature vector from the matrix is converted to a point in an object space—each point represents a different object. Optionally one or more classifiers, for instance supervised learning classifiers, are used to classify the objects in the ultrasonographic image as anatomical landmark(s) or as objects which are not anatomical landmark(s).

Figure 8:
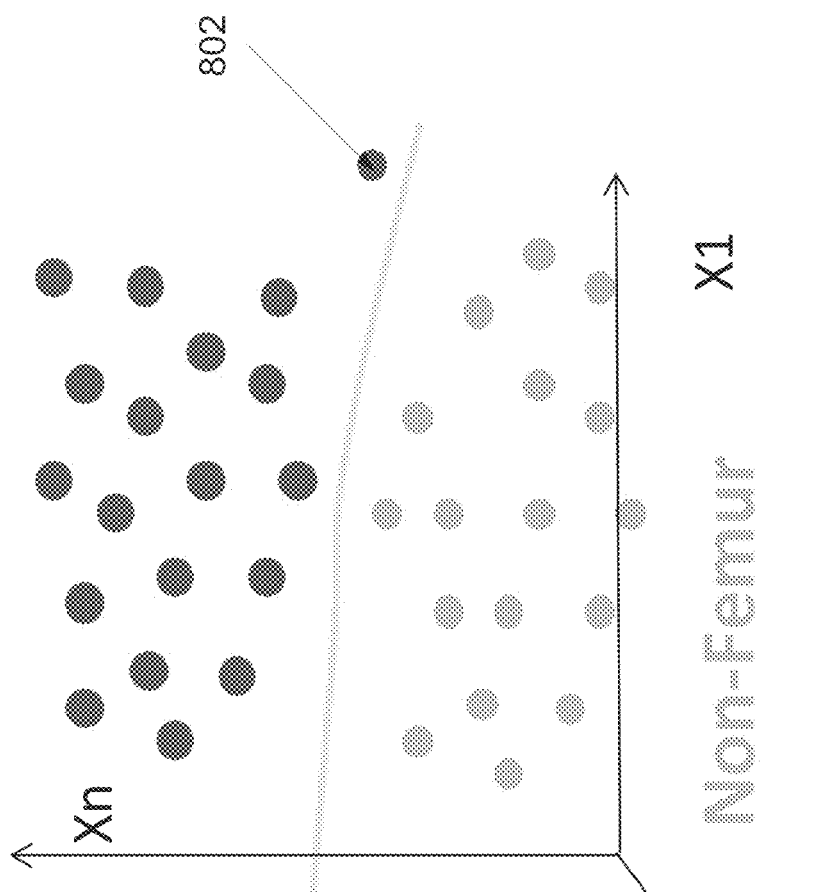

For example, the classification is determined based on a classification surface (threshold) that is defined in the object space. The classification surface is optionally learned during classifier training. For example, FIG. 8 is a schematic illustration of an object space and point 802 representing a segmented object. This segmented object is classified as an anatomic landmark, a femur, as it is above a classification surface 801.

The classification of the ultrasonographic image is now made based on the classification of the segmented object.

Optionally, a combined classifier may be used. This classifier combines classifiers of different anatomic landmarks and yields a classification of the ultrasonographic image directly. Optionally, the outcomes of classifiers of different anatomic landmarks are aggregated to form an anatomic landmark score vector. This vector is processed by a combination function to issue a determination of whether the image is classified as a genital plan or not.

Figure 9:
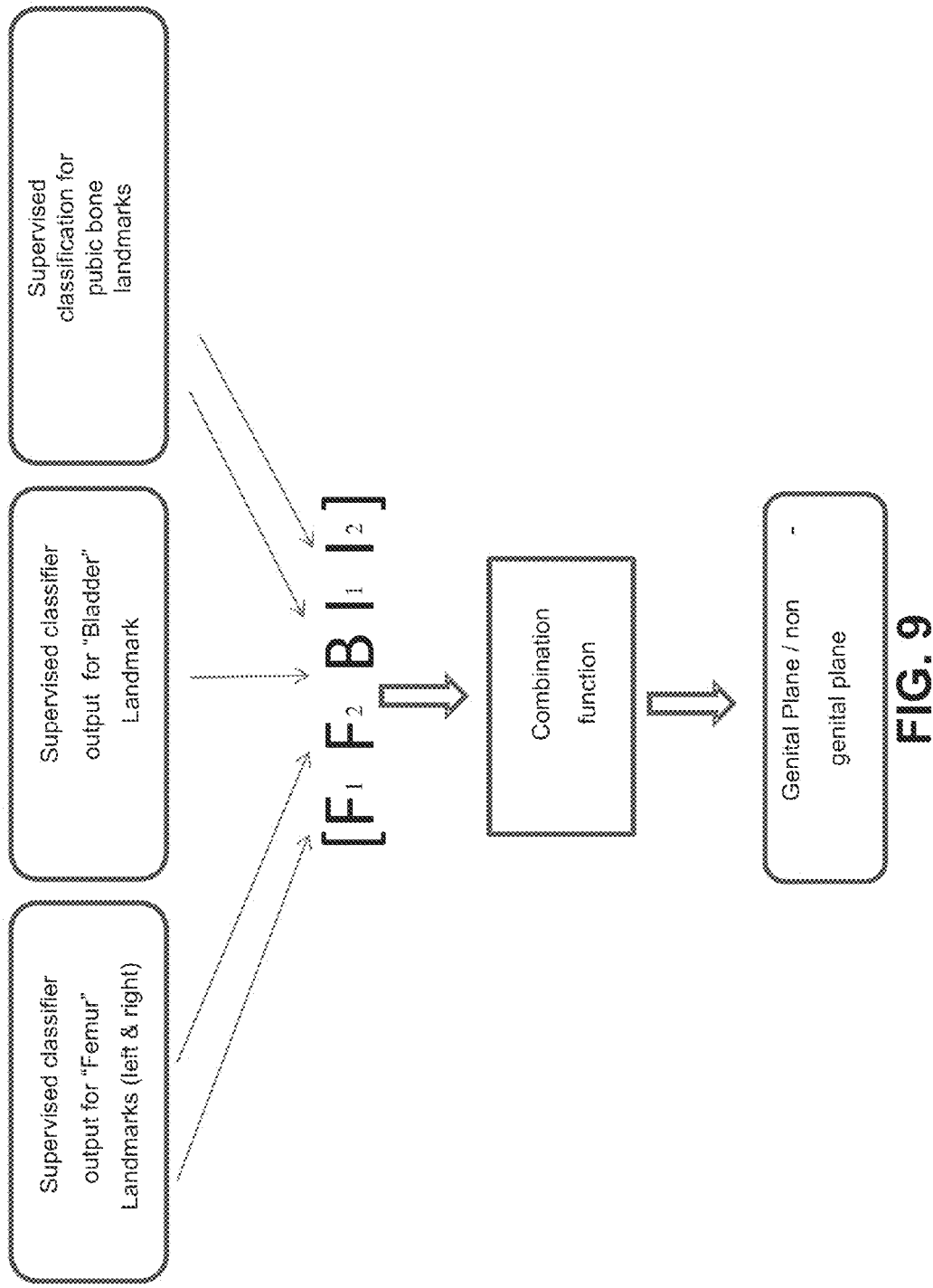

FIG. 9 is a flowchart depicting how valued scores given to an ultrasonographic image by classifiers of the following anatomical landmarks: a femur, a urinary bladder, and pelvic(s) bones are combined to form a score vector that is used by a combination function to classify an ultrasonographic image, according to some embodiments of the present invention.

Optionally, the combination function is a set of heuristic rules manually adapted to best fit a ground truth data labeling. For example, an ultrasonographic image is classified as follows:

Genital Plane=$[(F1>t1)\&(F2>t2)\&(B>t3)]|[(I1>t4)\& (I2>t5)\&(F1>t1)]|[(I1>t4)\&(F1>t1)\&(F2>t2)]| [(I1>t4)\&(I2>t5)\&(B>t3)]|[(I1>t4)\&(F1>t1)\& (B>t3)]$ where Genital Plane denotes a Boolean variable (1=femur,0=non femur) and F1, F2, B, I1, and I2 respectively denote different outputs of the landmark classifiers for left femur, right femur, urinary bladder, and pelvic bones and respectively denote Boolean and operator and Boolean or operator, t1,t2,t3,t4 and t5 respectively denote different thresholds empirically set on the output of the landmark classifiers for left femur, right femur, urinary bladder, and pelvic bones.

Reference is now made, once again, to FIG. 2. As shown at 204, if the ultrasonographic image was classified as a genital plan, the genital ROI is concealed in the presentation of the ultrasonographic image.

The concealment may be done by altering a portion of the ultrasonographic image by editing, masking, blurring, darkening, coloring, extracting, removing, trimming or manipulating and/or otherwise concealing the genital ROI.

The estimated location of the genital ROI in the ultrasonographic image is detected for concealment by localizing anatomical landmarks, such as the above described anatomical landmarks. The estimated location may be sized to cover a number of possible locations. The estimated location of the genital ROI is calculated based on predefined locational anatomical property(ies) of one or more anatomical landmarks. A predefined locational anatomical property may be a predetermined distance from the genitalia, a relative location (i.e. direction) to the genitalia, predetermined relative coordinates (a relative position), a relative size, a relative structure, a relative configuration, a relative density and/or texture descriptors and/or a relative shape. The predefined locational anatomical property is optionally extracted from an anatomical dataset that may be stored in the memory 133, for example a dataset associating between anatomical landmarks and their predefined locational anatomical properties. The predefined locational anatomical properties are based on anatomical knowledge about the expected range of distances between genitalia and the detected anatomical landmarks. This anatomical knowledge provides a set of constraints on the possible location of genitalia.

Figure 10:
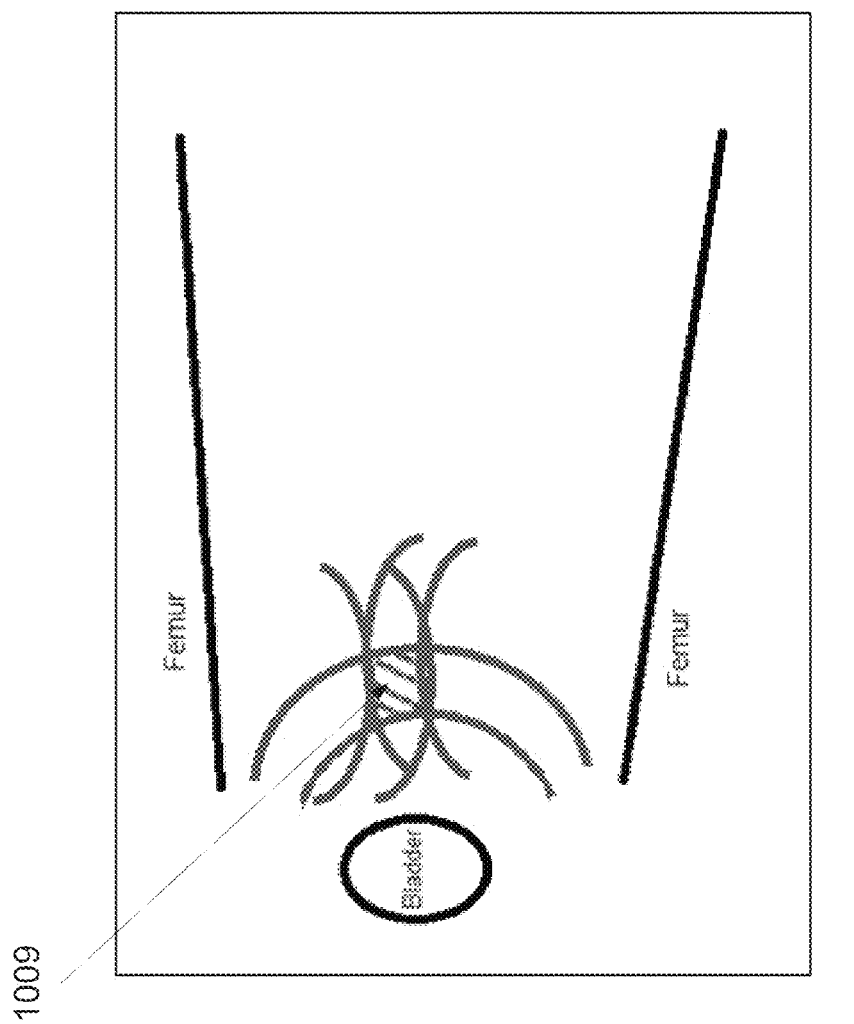

Optionally, the estimated location of the genital ROI is calculated by combining predefined locational anatomical properties of different anatomical landmarks. For example, the estimated location of the genital ROI is calculated based on the location of an intersection of areas defined by different distance ranges from different anatomical landmarks in the ultrasonographic image, for example anatomical landmarks identified as described above. For example, FIG. 10 is a schematic illustration depicting distance ranges from the urinary bladder, the left femur, and the right femur by pairs of aligned curved lines and an intersection 1099 of these distance ranges, according to some embodiments of the present invention.

A distance range is the distance at which the genital ROI is estimated to be from the anatomical landmark. For example, FIGS. 11A-11C are schematic illustrations of distance ranges from the left femur, the right femur and the urinary bladder. In schematic illustration, a plurality of consecutive and concentric contours which have been adapted to the shape of the respective anatomical landmark are depicted. The distance range is defined as the area between two consecutive and concentric contours, for example between 1101 and 1102. FIG. 11D depicts the ultrasonographic image and the intersection 1103 of areas defined by different distance ranges from different anatomical landmarks (the left femur, the right femur and the urinary bladder). FIG. 11E depicts the genital ROI that is calculated based on the location of the intersection.

Now, as shown at 205, the ultrasonographic image with the concealed genital ROI is presented during an evaluation of the fetus. This process is repeated for all or some of the ultrasonographic images which are captured during a fetal evaluation, allowing the operator, for example a physician, to perform a full fetal anatomy evaluation, for example second and third trimester fetal anatomy screening, without being exposed to the gender of the fetus.

Optionally, after the genital ROI is located as described above with reference to FIG. 2, changes in the location of the genital ROI are monitored by an object tracking algorithm. In such embodiments, the genital ROI remain concealed by estimating changes in the location of the genital ROI, for example in response to movement of the probe, movement of the pregnant woman or the fetus and/or the like. Optionally, the process depicted in FIG. 2 may be used for concealing another ROI based on the localization of anatomical landmarks which are outside of the ROI. For example, different organs may be concealed to focus to the physician attention during the evaluation and/or for marking the ROI during the screening.

As described above, ultrasonographic images may be 2D or 3D images. When 3D or 4D ultrasonographic images are used, a number of slices, namely a stack of slices, are acquired at once by the probe. The concealing in this case may be performed by applying the above described computerized method of concealing the genital ROI directly to each slice of the stack without making use of the fact that the relative position of the stack slices is known. In another embodiment, the data is considered as 3D or 4D and the anatomical landmarks defined for the 2D case are treated as 3D or 4D objects. In such embodiments, a hyperintensity segmentation map may be generated and used directly in 3D or 4D similarly to the described above. Optionally, a convex area becomes a convex volume defined as the object volume divided by its 3D or 4D convex hull volume. Once the features vectors are extracted from the 3D or 4D objects, supervised classification is applied in a similar fashion to the case of 2D objects for the detection of the landmarks.

The ROI is represented as a volume of interest (VOI) in 3D and may be directly defined by applying prior anatomical knowledge about relative position, orientation and/or distance range(s) from the genitalia to each landmark.

Reference is now made to FIGS. 12A-12E which are exemplary ultrasonographic images depicting coronal or tangential views of the genital ROI and anatomical landmarks. Reference is also now made to FIGS. 13A-13C which are exemplary ultrasonographic images depicting midsagittal views of the genital ROI and anatomical landmarks. Reference is also now made to FIGS. 14A-14C which are additional exemplary ultrasonographic images depicting a 3D views of the genital ROI and anatomical landmarks.

In these figures, F denotes Reference Femur/s, T denotes thigh's, Ur denotes urinary bladder, A denotes amniotic fluid, B denotes Pelvic bone/s including the Ischium, Pubis, Ilius or Sacrum bones, P denotes the Pelvis, Um denotes Umbilical cord, S denotes Spine, U denotes a the U shape of the thighs and pelvis, and LA denotes the anterior contour of the Trunk.

The methods as described above are used in the fabrication of integrated circuit chips.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant methods and systems will be developed and the scope of the term a probe, and an ultrasonographic image is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computerized method of adapting a presentation of ultrasonographic images during an ultrasonographic fetal evaluation, comprising:
    performing an analysis of a plurality of ultrasonographic images captured by an ultrasonographic probe during an evaluation of a fetus;
    automatically identifying a plurality of locations of a plurality of anatomical landmarks of at least one reference organ or tissue or body fluid of said fetus in said plurality of ultrasonographic images based on an outcome of said analysis;

automatically and indirectly localizing a region of interest (ROI), different than said plurality of anatomical landmarks, in at least some of said plurality of ultrasonographic images by:
- calculating for each of said plurality of anatomical landmarks, a plurality of consecutive contour lines encircling said each of said plurality of anatomical landmarks in a predefined plurality of different distances from a contour of said each of said plurality of anatomical landmarks,
- selecting for each of said plurality of anatomical landmarks, at least one contour line which is at least one of said plurality of consecutive contour lines according to a pre-determined distance,
- defining a region bound by intersections of said selected contour lines of said plurality of anatomical landmarks and
- determining said defined bound region as containing said region of interest (ROI); and concealing said bound region in a presentation of said at least some ultrasonographic images during said evaluation;

wherein said plurality of anatomical landmarks are imaged in said presentation and not concealed by said ROI.

2. The method of claim 1, wherein said ROI includes an image portion depicting the genitalia of said fetus.

3. The method of claim 1, further comprising providing an anatomical dataset associating between a plurality of predefined locational anatomical properties and a plurality of respective anatomical landmarks;

wherein said automatically localizing comprises selecting said predefined locational anatomical property from said plurality of predefined locational anatomical properties.

4. The method of claim 1, wherein said presentation is rendered while said ultrasonographic probe is manually maneuvered.

5. The method of claim 1, wherein said automatically identifying comprises identifying, from said plurality of ultrasonographic images, a group of ultrasonographic images wherein each member images a genital plan; said at least some ultrasonographic images are selected from said group.

6. The method of claim 5, wherein said automatically identifying comprises identifying said plurality of anatomical landmarks in each member of said group.

7. The method of claim 6, wherein each member of said group is identified by:
- segmenting a plurality of objects in said plurality of ultrasonographic images,
- identifying a plurality of anatomical features of each said object,
- substituting said plurality of anatomical features in a dataset, and
- classifying said member based on an analysis of said dataset.

8. The method of claim 7, wherein said classifying is performed by a classifier created by at least one classifier trained by supervised learning of a presence or absence of said plurality of anatomical landmarks.

9. The method of claim 7, wherein said classifying is performed by a plurality of classifiers set to calculate a score indicative of an estimate of a presence or absence of each of said plurality of anatomical landmarks.

10. The method of claim 7, wherein said automatically identifying is performed by calculating a form factor of at least one object depicted in said plurality of ultrasonographic images.

11. The method of claim 7, wherein said automatically identifying is performed by calculating a member of a group consisting of a convexity of at least one object depicted in said plurality of ultrasonographic images, a contour complexity of at least one object depicted in said plurality of ultrasonographic images, and texture descriptors of at least one object depicted in said plurality of ultrasonographic images.

12. The method of claim 1, wherein said automatically localizing is performed by a combination of a plurality of predefined locational anatomical properties taken from said plurality of anatomical landmarks.

13. The method of claim 1, wherein said predefined locational anatomical property is a range of distances between said plurality of anatomical landmarks and the genitalia of said fetus.

14. The method of claim 1, wherein said plurality of anatomical landmarks are selected from a group consisting of: at least one femur, at least one thigh, the pelvis, the spine, the U shape of thighs and pelvis, the anterior contour of the trunk, the urinary bladder, the Ischium, the Pubis, the Ilius, the Sacrum bones, the amniotic fluid, and the umbilical cord.

15. The method of claim 1, wherein said ultrasonographic images are slices from a stack used for three dimensional or four dimensional ultrasonographic imaging.

16. The method of claim 1, wherein said ROI is a volume and said ultrasonographic images are volumetric ultrasonographic images.

17. A system of adapting a presentation of ultrasonographic images during an ultrasonographic fetal evaluation, comprising:
- an interface which receives a plurality of ultrasonographic images captured by an ultrasonographic probe performing an evaluation of a fetus of a patient;
- a computerized processor; and
- a memory which comprises instructions to perform using said computerized processor, an analysis of a plurality of ultrasonographic images captured by an ultrasonographic probe during an evaluation of a fetus, to identify a plurality of anatomical landmarks of at least one reference organ or tissue or body fluid of said fetus based on an outcome of said analysis, to indirectly localize, based on at least one predefined locational anatomical property or texture descriptor of said plurality of anatomical landmarks, a region of interest (ROI), different than said plurality of anatomical landmarks, in said plurality of ultrasonographic images by calculating for each of said plurality of anatomical landmarks, a plurality of consecutive contour lines encircling said each of said plurality of anatomical landmarks in a predefined plurality of different distances from a contour of said each of said plurality of anatomical landmarks, selecting for each of said plurality of anatomical landmarks, at least one contour line which is at least one of said plurality of consecutive contour lines according to a pre-determined distance, defining a region bound by intersections of said selected contour lines of said plurality of anatomical landmarks and determining said defined bound region as containing said region of interest (ROI), and to conceal said bound region in a presentation of at least some of said plurality of ultrasonographic images during said evaluation;
wherein said plurality of anatomical landmarks are imaged in said presentation and not concealed by said ROI.

18. A computerized method of concealing a portion of an ultrasonographic image depicting genitalia of a fetus during an ultrasonographic fetal evaluation, comprising:
providing an anatomical dataset which is indicative of at least one predefined locational anatomical property of each of a plurality of anatomical landmarks of at least one reference organ or tissue or body fluid of said fetus;
performing an analysis of a plurality of ultrasonographic images captured by an ultrasonographic probe during an evaluation of a fetus;
selecting a group of ultrasonographic images from said plurality of ultrasonographic images such that each group member of said group depicts some of said plurality of anatomical landmarks;
localizing indirectly, in each group member of said group, a genital region of interest (ROI) which images the genitalia of said fetus, said localizing is performed according to respective said at least one predefined locational anatomical property of each of respective said some of said plurality of anatomical landmarks imaged in said member by calculating for each of said plurality of anatomical landmarks, a plurality of consecutive contour lines encircling said each of said plurality of anatomical landmarks in a predefined plurality of different distances from a contour of said each of said plurality of anatomical landmarks, selecting for each of said plurality of anatomical landmarks, at least one contour line which is at least one of said plurality of consecutive contour lines according to a pre-determined distance, defining a region bound by intersections of said selected contour lines of said plurality of anatomical landmarks and determining said defined bound region as containing said region of interest (ROI); and
concealing said bound region in a presentation of each member of said group during said evaluation;
wherein said some of said plurality of anatomical landmarks are imaged in said presentation and not concealed by said ROI.

19. The method of claim 1 further comprising tracking said ROI during said evaluation.

20. The method of claim 1 wherein said ROI is a plurality of different regions of interests, different from said plurality of anatomical landmarks.

* * * * *